(12) United States Patent
Weymarn-Schärli

(10) Patent No.: US 9,931,191 B2
(45) Date of Patent: Apr. 3, 2018

(54) DEVICE, ESPECIALLY TUBE OR CATHETER, FOR AT LEAST PARTIALLY INTRODUCING INTO A BODY PASSAGE

(76) Inventor: Alexander Von Weymarn-Schärli, Basel (CH)

(*) Notice: Subject to any disclaimer, the term of this patent is extended or adjusted under 35 U.S.C. 154(b) by 829 days.

(21) Appl. No.: 13/532,523

(22) Filed: Jun. 25, 2012

(65) Prior Publication Data

US 2012/0265131 A1 Oct. 18, 2012

Related U.S. Application Data

(63) Continuation of application No. 10/578,130, filed as application No. PCT/CH2004/000635 on Oct. 22, 2004, now abandoned.

(51) Int. Cl.
*A61F 5/14* (2006.01)
*A61F 2/04* (2013.01)
*A61M 25/00* (2006.01)
*A61M 25/01* (2006.01)

(52) U.S. Cl.
CPC ........... *A61F 2/04* (2013.01); *A61M 25/0043* (2013.01); *A61M 25/01* (2013.01); *A61F 2210/009* (2013.01); *A61F 2250/0003* (2013.01); *A61F 2250/0004* (2013.01); *A61F 2250/0063* (2013.01); *A61M 25/0045* (2013.01); *A61M 2025/0004* (2013.01); *A61M 2025/0039* (2013.01); *A61M 2025/0063* (2013.01)

(58) Field of Classification Search
CPC ...... A61M 25/0043; A61M 25/01; A61F 2/04

USPC ......................................................... 604/349
See application file for complete search history.

(56) References Cited

U.S. PATENT DOCUMENTS

| 4,619,643 A | * | 10/1986 | Bai | ............................... 604/43 |
| 5,542,938 A | * | 8/1996 | Avellanet et al. | ............ 604/528 |
| 6,203,525 B1 | * | 3/2001 | Whayne et al. | ........... 604/95.01 |

\* cited by examiner

*Primary Examiner* — Tatyana Zalukaeva
*Assistant Examiner* — Andrew J Mensh
(74) *Attorney, Agent, or Firm* — Bruce L. Adams; Klintworth & Rozenblat IP LLP

(57) ABSTRACT

The invention relates to a device (1), especially a tube or a catheter, for at least partially introducing into a body passage, said device comprising a long outer envelope body (10), a long inner body (11) that is partially peripherally surrounded by the envelope body (10), and a device (12) by which means the possibility of a relative movement between the envelope body (10) and the inner body (11) is enabled or impeded in a targeted, controllable manner. According to the invention, the control device (12) is formed by the arrangement and embodiment of the envelope body (10) and the inner body (11) and comprises no additional mechanical means in the annular intermediate region (13) between said two bodies (10, 11). Preferably, the control device is embodied in such a way that it acts on the friction between the envelope body and the inner body (10, 11).

6 Claims, 2 Drawing Sheets

Figure 1:
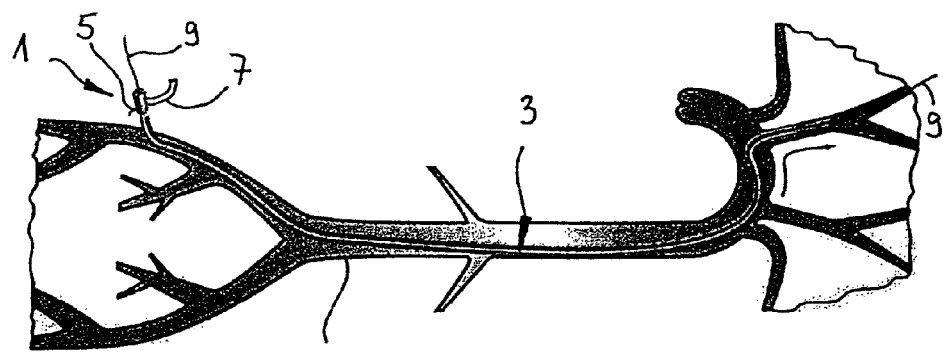

DEVICE, ESPECIALLY TUBE OR CATHETER, FOR AT LEAST PARTIALLY INTRODUCING INTO A BODY PASSAGE

CROSS-REFERENCE TO RELATED APPLICATIONS

This application is a continuation of application Ser. No. 10/578,130 filed May 2, 2006 and now abandoned, which is a U.S. national stage application of copending International Application No. PCT/CH 2004/000635, filed Oct. 22, 2004, claiming an earliest priority date of Nov. 3, 2003, and published in a non-English language.

The invention relates to a device, especially a tube or a catheter, for at least partially introducing into a body passage in accordance with the preamble to Patent Claim 1.

Devices of this kind are introduced, for example, into a vessel, such as a vein or an artery. A device executed in the form of a so-called tube can exhibit an applicator, also known as an introducer, as well as a haemostatic valve. Long tubes are used, for example, in the treatment of vessels in the brain. This requires a long route to be taken through the point of access to the vessels in the groin as far as the vessels in the brain. The vessels along this route often adopt tight convolutions in older people. This results in reduced controllability and guidability of the tube in question or the catheter in question, or even a stent.

During its insertion and introduction, the device in question should ideally be flexible in order to be able to pass easily through all the convolutions. On the other hand, once the tip of the tube is present at the desired site, it would be more helpful to have a device with greater rigidity, to enable the therapy material to be brought reliably to the therapy site. A soft device, such as a tube, can often spring back in the arch of the aorta, however, so that precise positioning of the therapy material, for example a stent, is made more difficult.

Previously disclosed in DE 43 16 330 A1 is a guide wire intended for medical applications, which is used to introduce catheters, tubes or the like into the human body. This guide wire is produced in a single piece from an elastic material and has an initial thickness, at least one reduced cross section in conjunction therewith, and at least one section with a cross section corresponding to the first thickness.

Previously disclosed in U.S. Pat. No. 6,015,402 is a stent with a polygonal, namely hexagonal, cross section.

DE 35 30 310 C2 discloses a guide wire for catheters for blood vessels, which exhibits a polygonal cross section and a stiffening core. The latter terminates a certain distance before the end of the guide wire that is remote from the investigator.

Also previously disclosed in EP 0 773 037 A2 is a device, referred to as a guide wire unit, which consists of an envelope body and an inner body present therein, the cross sections of which are formed in such a way as to eliminate mutual distortion or twisting of the aforementioned bodies. The inner body is thus prevented from rotating relative to the envelope body by reason of the non-circular, mutually interacting cross sections.

Previously disclosed in DE 41 13 265 A1 is a device in accordance with the preamble to Patent Claim 1. This device has an insertion part, which exhibits an inner wall, an outer wall and an annular intermediate region formed between these. Also provided is a connection for the introduction and evacuation of a fluid respectively into and from the entire intermediate region. Supporting bodies are provided in the intermediate region, so that, in conjunction with the evacuation of the intermediate region, the insertion part is stiffened in whatever form it has adopted before the evacuation.

The object of the invention is to make available a device of the aforementioned kind, which is executed in a simpler and more space-saving manner.

This object is achieved in accordance with the invention by a device having the characteristic features of Patent Claim 1. Advantageous further developments are the subject of the dependent Claims.

In accordance with the invention, the control device is itself formed by the arrangement and embodiment of the envelope body and the inner body and comprises no additional mechanical means in the annular intermediate region between the envelope body and the inner body. In this respect, contrary to the last-mentioned state of the art, the device in accordance with the invention can exhibit a smaller overall diameter, since the supporting bodies referred to in the state of the art, which are executed, for example, as opposing teeth or flutings, do not in actual fact require to be made available in accordance with the invention. Rather, the device in accordance with the invention and its control device takes advantage of the arrangement and embodiment of the envelope body and the inner body and is able in this respect to dispense entirely with additional mechanical means in the annular intermediate region between the envelope body and the inner body. If a relative movement between the bodies is impeded or excluded by means of the control device, this ultimately provides stiffening of the entire device, so that the therapy material can be brought reliably to the therapy site, without encountering the risk of the device slipping out of the target vessel, for example. The device in accordance with the invention is consequently sufficiently flexible by permitting a relative movement between the envelope body and the inner body, and is adequately rigid by impeding or preventing such relative movement between the bodies. The device in accordance with the invention can be introduced particularly gently into a body passage, and it is also capable, in view of its construction, unlike the previously disclosed device in accordance with the last-mentioned state of the art, of being introduced into body passages of relatively small diameter. Moreover, the deformability of the device in accordance with the invention can be improved in its non-stiffened normal state in comparison with the last-mentioned state of the art, as there is also no possibility of unintentional hooking or toothed engagement in the intermediate region between the envelope body and the inner body.

In accordance with one advantageous further development, the control device is embodied in such a way that it acts on the friction between the envelope body and the inner body, so that a relative movement between the aforementioned bodies can be impaired or entirely prevented through an increase in the friction.

The control device is advantageously embodied in such a way that the friction between the envelope body and the inner body is controllable mechanically and/or by means of pressure or vacuum, electrical polarization, magnetization and/or by means of a molecular change. In this respect, the control device can be adapted to the application in each particular case and can be made differently, for example in the case of a device executed in the form of a long tube, than in the case of a device executed in the form of a short tube. It is also possible, however, to execute the control device as a combination of a plurality of friction-controlling means.

In accordance with one advantageous embodiment of the invention, the material of the envelope body and the inner body is formed in a flexible, yet torsionally resistant manner, and the envelope body and the inner body in each case exhibit a preferably polygonal cross section, such that the envelope body and the inner body are capable of being caused to rotate relative to one another by means of the control device in such a way that the inner body makes contact at least partially with the envelope body. In this embodiment, the control device is also formed relatively simply as a mechanical means. The friction between the said bodies is increased, and relative movement between the said bodies is at least impaired in this way through the at least partial contact of the inner body with the envelope body. This contributes to the stiffening of the entire device. Moreover, the aforementioned step for the purpose of stiffening the device can also be reversed rapidly, by causing the envelope body and the inner body to rotate back again into their position in which they are not twisted in relation to one another. In the last-mentioned case, the device is once more adequately flexible and supple.

In accordance with a further development of the invention, the envelope body and the inner body in each case are of hexagonal execution, are arranged concentrically to one another and are dimensioned in such a way that the inner body, with the bodies in their mutually rotated state, makes contact preferably with all of its corners with an inner wall of the envelope body. It is therefore possible in this embodiment ultimately to increase the friction at six at least linear points. The inner body and the envelope body become jammed against one another in this way, whereby the inner friction is increased and the shaft of the device, for example the shaft of the tube, is stiffened.

In accordance with another embodiment of the invention, a pressure medium, preferably compressed air, can be introduced, or a vacuum can be applied, by means of the control device in/at the intermediate region between the envelope body and the inner body. With the help of a control device of this kind, the flexibility and the stiffening of the entire device can be adjusted and changed particularly quickly. Compressed air in particular is readily available in the buildings in which interventions of this kind are undertaken.

In accordance with a further embodiment of the invention, the control device and the envelope body as well as the inner body are embodied in such a way that magnetic fields of different polarity are capable of being generated along the envelope body and along the inner body for the selective production of a mutual attraction of the bodies, whereby preferably the envelope body and the inner body are manufactured from a magnetizable material, especially a soft magnetic material, or are provided with a magnetizable coating. Through the mutual attraction or repulsion of the bodies, the friction between these can also be influenced effectively.

In accordance with a further embodiment, the magnetic fields are capable of being generated by the application of an electrical voltage to the envelope body and the inner body. A plurality of means is thus available for the embodiment of the control device for the effective influencing of the friction between the envelope body and the inner body, whereby the choice of the most suitable control device that is best suited to the application in each case is facilitated.

Figure 2:
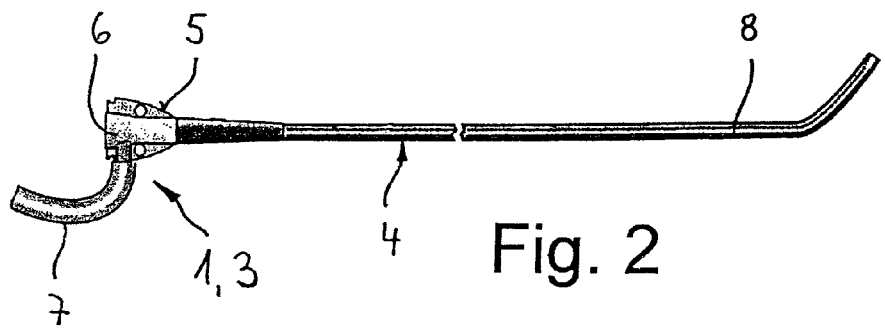
Figure 3:
Figure 4:
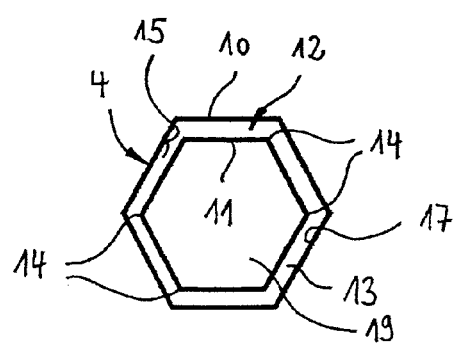
Figure 5:
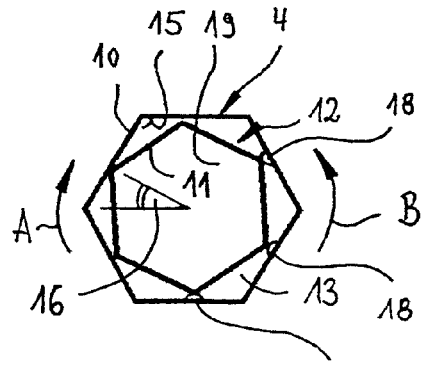
Figure 6:
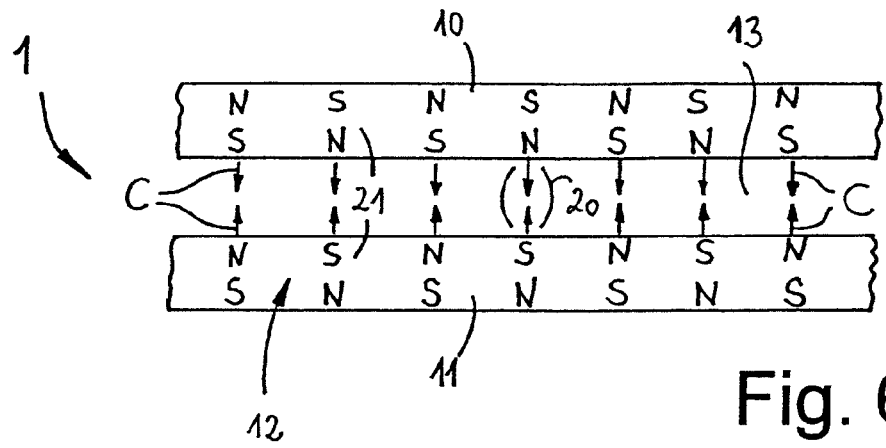
Figure 7:
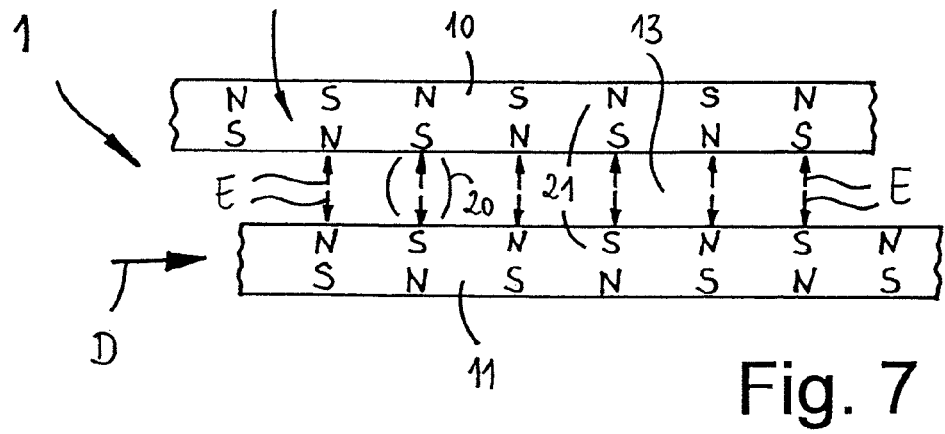
Figure 8:
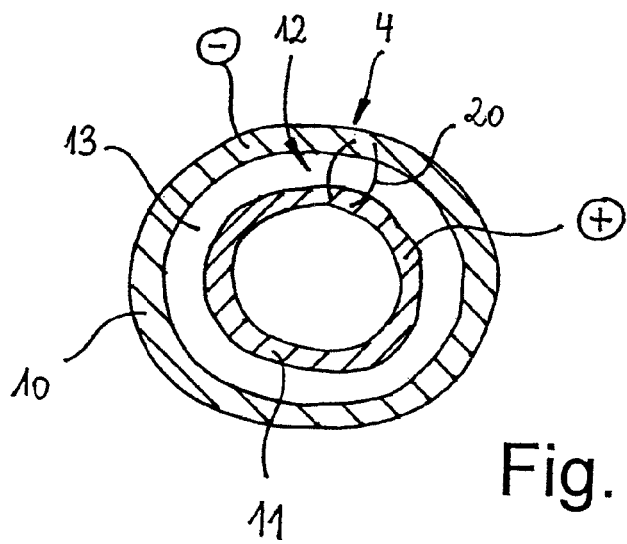

Various embodiments of the subject of the invention are described below in greater detail with reference to the accompanying drawings, in conjunction with which all the characteristic features that are described and/or represented as illustrations individually or in a desired combination constitute the subject of the present invention, regardless of their inclusion in the Claims or their relationship. The drawings show:

FIG. 1 a schematic, partial representation of vessels with a device partially introduced therein;

FIG. 2 a schematic view from above of a device executed in the form of a tube;

FIG. 3 a schematic view from above of a part of the device in accordance with FIG. 2;

FIG. 4 a schematic cross section through the device in the position in which the bodies are not twisted in relation to one another;

FIG. 5 a schematic representation of the device in accordance with FIG. 4 in the position in which the bodies are twisted in relation to one another;

FIG. 6 a schematic, partial view from the side of the device, in which the parts are shown clearly separated from one another;

FIG. 7 a schematic view from the side of the part of the device shown in FIG. 6, in which the parts are separated from one another and are shown offset in relation to one another; and FIG. 8 a schematic cross section through a device in accordance with another embodiment.

It should be pointed out at this juncture that the hatchings symbolizing a cut in FIGS. 1, 2, 4 to 7 have been omitted in the interests of clarity.

Illustrated schematically in FIG. 1 is a device 1 intended for medical applications, namely a tube 3, for example, which is partially introduced in a body passage 2. The device can also be executed as a catheter. The body passage 2 shown in FIG. 1 is a part of a vessel, for example a vein or an artery. It is obvious that the body passage 2 in FIG. 1 is shown only in highly simplified form.

The device 1 executed as a tube 3 permits access for a specific period into the body passage 2 in the form of a vessel, but without too much blood flowing from the vessel as a result. The return flow of the fluid is stopped, in spite of the fact that a catheter, for example, is being moved back and forth inside the tube 3.

Unlike what is shown in FIG. 1, the vessels usually become broader with age, so that they ultimately adopt more convolutions and exhibit more cavities. The device in accordance with the invention should be adequately flexible when it is inserted into the vessel, so that it is able to follow all the curves of the vessel. Once the device has been positioned, however, it should then be as rigid as possible, so that it forms a good guide for a catheter, for example.

As indicated in FIG. 2, the device 1 in accordance with the invention is executed in the form of the tube 3 having a long and narrow outer body 4, for example, at the operator's end 5 of which a haemostatic valve 6 and a so-called side port 7 are present. The side port 7 is used, for example, for the internal flushing of the long and narrow outer body 4. Present in the long and narrow outer body 4 is a so-called applicator, also known as an introducer 8, which almost fills the lumen of the long and narrow outer body 4 and stiffens the outer body 4 for the purpose of introducing the device 1 into the body passage 2.

Also present in the body passage 2 in question, in accordance with FIG. 1, is a so-called guide wire 9, which passes through the tube 3 and, as indicated in FIG. 1, exits from this at the rear end 5 close to the operator and at the front end of the tube 3. In the interests of clarity, the guide wire 9 is omitted in the representation of the tube 3 in FIG. 2. The guide wire 9 serves as an aid, along which the device 1 in accordance with the invention is capable of being pushed into the target vessel.

The aforementioned introducer 8 permits a smooth transition between the difference in the diameter or calibre from the diameter of the guide wire 9 to the diameter of the long and narrow outer body 4.

In accordance with FIGS. 4, 5 and 8, the device 1 in accordance with the invention possesses the outer body 4, which exhibits a long and narrow external envelope body 10 and a long and narrow inner body 11 at least partially peripherally surrounded by the envelope body 10. The device 1, in the form of the tube 3 in the selected illustrative embodiment, is thus of double-walled execution.

A device 12 allocated to the envelope body 10 and/or to the inner body 11 is also provided, by means of which the possibility of a relative movement between the envelope body 10 and the inner body 11 is enabled, or at least impeded, in a targeted, controllable manner.

In accordance with the invention, the control device 12 is itself formed by the arrangement and embodiment of the envelope body 10 and the inner body 11 and comprises no additional mechanical means in the annular intermediate region 13 between the envelope body and the inner body 10, 11.

The control device 12 is embodied in such a way that it acts on the friction between the envelope body 10 and the inner body 11, whereby the intermediate region 13 between the envelope body 10 and the inner body 11 in the representation in accordance with FIGS. 4, 5 and 8 is represented as a greatly enlarged view in the interests of clarity.

In accordance with the embodiments illustrated in FIGS. 4 to 8, the control device 12 is executed in such a way that the friction between the envelope body and the inner body 10, 11 is controllable mechanically and/or by means of pressure or vacuum, electrical polarization, magnetization and/or by means of a molecular change. It follows, therefore, that the control device 12 depends on one of the aforementioned steps or on a combination of several steps.

In accordance with a first embodiment of the invention, which is illustrated in FIGS. 4 and 5, the material is formed in a flexible, yet torsionally resistant manner by the envelope body 10 and the inner body 11. The envelope body 10 and the inner body 11 in each case exhibit a preferably polygonal cross section in such a way that the envelope body 10 and the inner body 11 are capable of being caused to rotate relative to one another by means of the control device 12, so that the inner body 11 makes contact at least partially with the envelope body 10. In this case, rotation of the inner body 11 in the direction of the arrow A or in the direction of the arrow B, for example, can take place relative to the envelope body 10 (see FIG. 5).

As shown in FIGS. 4 and 5, the envelope body 10 and the inner body 11 are of hexagonal execution in each case and are arranged concentrically to one another. Moreover, they are dimensioned in such a way that the inner body 11, with the bodies 10, 11 in their mutually rotated state, makes contact at all of its six corners 14 with an inner wall 15 of the envelope body 10. The envelope body and the inner body 10, 11 are shown in FIG. 4 in the state in which they are not rotated in relation to one another, and in FIG. 5 in the state in which they are rotated in relation to one another.

The rotation of the inner body 11 can take place over an angle 16 of not quite 30°, for example. It is clear that the angle will be smaller as the thickness of the intermediate regions 13 decreases.

As indicated in FIG. 5 in the right-hand area only, a plurality of longitudinally oriented ribs 18, preferably spaced apart uniformly over the internal extent 17 of the inner wall 15, are provided on the inner wall 15 of the envelope body 10. The ribs 18 in this case are arranged and executed in such a way that the corners 14 of the inner body 11 make contact with the ribs in the event of the rotation of the inner body in the direction of the arrow A or of the arrow B.

In accordance with another embodiment, not illustrated here in greater detail, a pressure medium, preferably compressed air, is capable of being introduced by means of the control device 12 into the intermediate region 13 between the envelope body and the inner body 10, 11, or a vacuum can be applied to the intermediate region 13. In this case, at least one of the aforementioned bodies is manufactured from an extensible material. The increase in the friction between the envelope body and the inner body 10, 11 takes place in the last-mentioned case through the close, two-dimensional contact of the inner body 11 with the inner wall 15 of the envelope body 10. In this case, the control device can be formed in such a way, for example, that the intermediate region 13 between the envelope body and the inner body 10, 11 is evacuated, or that the inner space 19 of the inner body 11 is exposed to the pressure medium, extends in a radial direction and makes two-dimensional contact with the inner wall 15 of the envelope body 10.

In accordance with further embodiments of the invention, which are represented schematically on the one hand in FIGS. 6 and 7 and on the other hand in FIG. 8, the control device 12 and the envelope body as well as the inner body 10, 11 are executed in such a way that magnetic fields 20 of different polarity 21 are capable of being generated along the envelope body 10 and along the inner body 11 for the selective production of a mutual attraction of the bodies 10, 11.

In accordance with the embodiment of the invention represented in FIGS. 6 and 7, the magnetic fields are capable of being generated not only within each of the bodies 10, 11, but also from one body to the other in a permanently magnetic fashion, whereby, as illustrated in detail in a side view of the device 1 in accordance with FIG. 6, the individual bodies are separated from one another over the intermediate region 13, and each of the bodies 10, 11 is reverse polarized alternately along its length and in a radial direction. As a result, a mutual attraction of the bodies 10, 11, as indicated by the arrows. C facing towards one another in FIG. 6, is produced for an axial arrangement of the bodies in accordance with FIG. 6.

If, as indicated in FIG. 7, for example, the inner body 11 in is now displaced relative to the envelope body 10 in an axial direction in the direction of the arrow D, the bodies 10, 11 will be repelled from one another, since like polarities are situated opposite one another in the bodies. This is indicated by the arrows E facing away from one another in FIG. 7. It is clear that the effect of the mutual repulsion of the bodies illustrated in FIG. 7 based on the arrangement in accordance with FIG. 6 can also be achieved by causing the envelope body 10 to be displaced relative to the inner body 11 in an axial direction.

The different polarity 21 of the envelope body 10 and the inner body 11 is indicated in FIGS. 6 and 7, for example, by the letters "N" and "S", and in FIG. 8 by the designation "+" or "−", whereby "N" stands for the North pole and "S" for the South pole of the magnetic field, and "+" and "−" stand for a positive and negative electrical charge.

The polarities indicated in FIGS. 6 and 7 by the designations "N" and "S" first pass inside each body, as already described above, and then from one body to the other.

The envelope body and the inner body 10, 11 are manufactured in accordance with a preferred embodiment of the invention from a magnetizable material, especially a soft magnetic material, or are provided with a magnetizable coating (not illustrated here in greater detail).

The bodies 10, 11 in the embodiment of FIGS. 6 and 7 are in the form of permanent magnets.

In the embodiment of the invention shown in FIG. 8, both the envelope body 10 and the inner body 11 have a more or less circular cross section. In this embodiment, too, it is clear that the intermediate region 13 illustrated between the envelope body 10 and the inner body 11 is greatly enlarged, and that the external diameter of the inner body 11 is in practice only slightly smaller than the internal diameter of the envelope body 10. If desired, a lubricant fluid can also be present in the annular intermediate region 13. It is also possible, however, to omit such a lubricant fluid.

In the embodiment illustrated in FIG. 8, the magnetic fields 20 can be generated by the application of an electrical voltage to the envelope body and the inner body 10, 11.

In the event that a pressure medium can be introduced into the device, or that a vacuum can be applied to the device by means of the control device, the pressure medium can be applied, for example, in the interior space 19 of the inner body. It is also possible to make the inner body of double-walled execution and in this way, for example, to impart radial stretching to the inner body by causing it to inflate.

In the case of magnetic fields, these can be built up and reduced not only via the material of the envelope body and the inner body, for example, but also via a magnetizable liquid.

Finally, all the embodiments serve to influence the friction between the envelope body and the inner body in the desired way in a simple and space-saving manner.

A device, especially a medical device, is created in this way, which is capable of and executed for simpler and more space-saving operation, and above all is sufficiently flexible on the one hand, but is also adequately rigid on the other hand, depending on which state is desired in practice.

What is claimed is:

1. A sheath for at least partial introduction into a body passage, comprising: an envelope body inside of which is an inner body with an annular space between the two bodies, wherein the inner body and the envelope body have polygonal cross sections and are rotationally movable relative to one another to bring the inner body into contact with the envelope body thereby imparting stiffness to the sheath, wherein the inner body and the outer body each have plural sidewalls that define the polygonal cross sections, and wherein corners of adjoining sidewalls of the inner body can be brought into contact with sidewalls of the envelope body to impart the stiffness to the sheath, and the sidewalls of the inner body and the envelope body can be situated parallel to each other to impart flexibility to the sheath.

2. A sheath according to claim 1; wherein the polygonal cross sections of the inner and envelope bodies have the same shape.

3. A sheath according to claim 1; wherein the arrangement of the envelope body and the inner body forms a control device that controls relative rotational movement of the inner and envelope bodies.

4. A sheath for at least partial introduction into a body passage, comprising: an envelope body inside of which is an inner body with an annular space between the two bodies, the inner and envelope bodies being movable relative to one another to impart flexibility to the sheath; wherein the envelope body and the inner body are manufactured from magnetizable material for selectively creating magnetic attraction forces of opposite polarity between the inner body and the envelope body at spaced-apart locations along the lengths thereof within the body passage to restrain relative movement between the inner and envelope bodies to impart stiffness to the sheath.

5. A sheath according to claim 4; wherein the magnetizable material comprises magnetized regions of the inner and envelope bodies that are alternately oppositely polarized along the lengths of the inner and bodies.

6. A sheath according to claim 4; wherein the magnetizable material is disposed outside of, and not within, the annular space between the inner and envelope bodies.

* * * * *